United States Patent
Nelson et al.

(10) Patent No.: US 8,098,373 B2
(45) Date of Patent: Jan. 17, 2012

(54) SPATIALLY AND SPECTRALLY PARALLELIZED FIBER ARRAY SPECTRAL TRANSLATOR SYSTEM AND METHOD OF USE

(75) Inventors: Matthew Nelson, Harrison City, PA (US); Patrick Treado, Pittsburgh, PA (US); Ryan Priore, Wexford, PA (US)

(73) Assignee: Chemimage Corporation, Pittsburgh, PA (US)

( * ) Notice: Subject to any disclaimer, the term of this patent is extended or adjusted under 35 U.S.C. 154(b) by 0 days.

(21) Appl. No.: 12/759,082

(22) Filed: Apr. 13, 2010

(65) Prior Publication Data

US 2010/0265502 A1    Oct. 21, 2010

Related U.S. Application Data

(60) Provisional application No. 61/169,364, filed on Apr. 15, 2009.

(51) Int. Cl.
*G01J 3/28* (2006.01)
(52) U.S. Cl. ............................................. 356/328
(58) Field of Classification Search ............. 356/300, 356/301, 317, 326, 328
See application file for complete search history.

(56) References Cited

U.S. PATENT DOCUMENTS

| | | | |
|---|---|---|---|
| 5,615,673 A * | 4/1997 | Berger et al. | ............ 600/326 |
| 7,440,096 B2 | 10/2008 | Gardner | |
| 7,471,386 B2 | 12/2008 | Neiss | |
| 7,471,389 B2 | 12/2008 | Tuschel | |
| 7,474,395 B2 | 1/2009 | Nelson | |
| 7,480,033 B2 | 1/2009 | Treado | |
| 7,626,696 B2 | 12/2009 | Zhang | |
| 2010/0148073 A1 | 6/2010 | Nelson | |

* cited by examiner

*Primary Examiner* — Tarifur Chowdhury
*Assistant Examiner* — Abdullahi Nur (57) ABSTRACT

System and method for spatially and spectrally parallelized FAST. A sample is illuminated to thereby produce interacted photons. The photons are passed through a filter and received at a two-dimensional end of a FAST device wherein said FAST device comprises a two-dimensional array of optical fibers drawn into a one-dimensional fiber stack so as to effectively convert a two-dimensional array of optical fibers into a curvilinear field of view, and wherein said two-dimensional array of optical fibers is configured to receive said photons and transfer said photons out of said fiber array spectral translator device and to a spectrograph through said one-dimensional fiber stack wherein said one-dimensional fiber stack comprises at least two columns of fibers spatially offset in parallel at the entrance slit of said spectrograph. The photons are then detected at a detector to thereby obtain a spectroscopic data set representative of the sample.

15 Claims, 6 Drawing Sheets

SPATIALLY AND SPECTRALLY PARALLELIZED FIBER ARRAY SPECTRAL TRANSLATOR SYSTEM AND METHOD OF USE

RELATED APPLICATIONS

This application claims priority to U.S. Provisional Application No. 61/169,364, filed on Apr. 15, 2009, entitled "Spatially and Spectrally Parallelized FAST", which is hereby incorporated by reference in its entirety.

BACKGROUND

Chemical imaging has a powerful capability for material characterization, process monitoring, quality control and disease-state determination. Chemical imaging combines digital imaging and molecular spectroscopy techniques, which can include Raman scattering, fluorescence, photoluminescence, ultraviolet, visible and infrared absorption spectroscopes, among others.

A Fiber Array Spectral Translator (referred to herein as "FAST", "FAST fiber bundle", "FAST array", and/or "FAST device") device when used in conjunction with a photon detector allows massively parallel acquisition of full-spectral images. A FAST device can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional ("2D") array on one end and a one dimensional ("1D") array (i.e., linear) array on the other end. The linear array is useful for interfacing with a spectrograph and a photon detector, such as a charge-coupled device ("CCD"). The two-dimensional array end of the FAST is typically positioned to receive photons from a sample. The photons from the sample may be, for example, absorbed by the sample, emitted by the sample, reflected off the sample, refracted by the sample, fluoresced from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrograph of a photon detector, such as a charge-coupled device so as to apply the photons received at the two-dimensional end of the FAST detector rows of the photon detector. Software may be used to extract the spectral/spatial information that is embedded in a single CCD image frame.

One advantage of this type of apparatus over other spectroscopic apparatus is speed of analysis. A complete spectrographic imaging data set can be acquired in the amount of time it takes to generate a single spectrum from a given material. Additionally, the FAST device can be implemented with multiple detectors. The FAST device allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end input into the entrance slit of a spectrograph.

FAST holds potential for acquiring hundreds to thousands of full spectral range, spatially-resolved spectra, such as Raman spectra, substantially simultaneously. Therefore, a FAST device may be used in a variety of situations to help resolve difficult spectrographic problems.

Despite its potential for quick acquisition of images, traditional FAST suffers from low fidelity imaging. Spatial parallelization of FAST allows for more fibers to be imaged at the entrance slit of a dispersive spectrograph. This is accomplished by placing more than one column of fibers spatially offset in parallel at the entrance slit. Spatial parallelization of FAST, however, introduces spectrally overlapping regions between dispersed columns of fibers at the detector focal plane. Therefore, there exists a need for a system and method that provides for quick image acquisition without spectral overlap.

SUMMARY

The present disclosure provides for a system and method that overcomes the limitations and shortcomings of the prior art and provides for high fidelity imaging. The present disclosure provides for spatial and spectral parallelization of FAST by using a filter and placing more than one column of fibers spatially offset in parallel at the entrance slit of a spectrograph. This holds potential for significantly increasing the number of fibers, and therefore image pixels, in the reconstruction image without spatial overlap.

DETAILED DESCRIPTION

Reference will now be made in detail to the embodiments of the present disclosure, examples of which are illustrated in the accompanying drawings. Wherever possible, the same reference numbers will be used throughout the specification to refer to the same or like parts.

The present disclosure relates to spectroscopic systems, particularly fiber array spectral translator ("FAST") spectroscopic systems, and more particularly to a system and method for overcoming the low image fidelity associated with the prior art. FAST technology can acquire a few to thousands of full spectral range, spatially resolved spectra simultaneously. This may be done by focusing a spectroscopic image onto a two-dimensional array of optical fibers that are drawn into a one-dimensional distal array with, for example, serpentine ordering. The one-dimensional fiber stack is coupled to an imaging spectrograph. A microprocessor and/or software may be used to extract spectral/spatial information that is embedded in a single charge-coupled device ("CCD") image frame.

One of the fundamental advantages of this method over other spectroscopic methods is speed of analysis. A complete spectroscopic imaging data set can be acquired in the amount of time it takes to generate a single spectrum from a given material. FAST can be implemented with multiple detectors.

Color-coded FAST spectroscopic images can be superimposed on other high-spatial resolution gray-scale images to provide significant insight into the morphology and chemistry of the sample.

The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end. The distal end feeds the optical information into associated detector rows. The detector may be a CCD detector having a fixed number of rows with each row having a predetermined number of pixels. For example, in a 1024-width square detector, there will be 1024 pixels (related to, for example, 1024 spectral wavelengths) per each of the 1024 rows.

Figure 1:
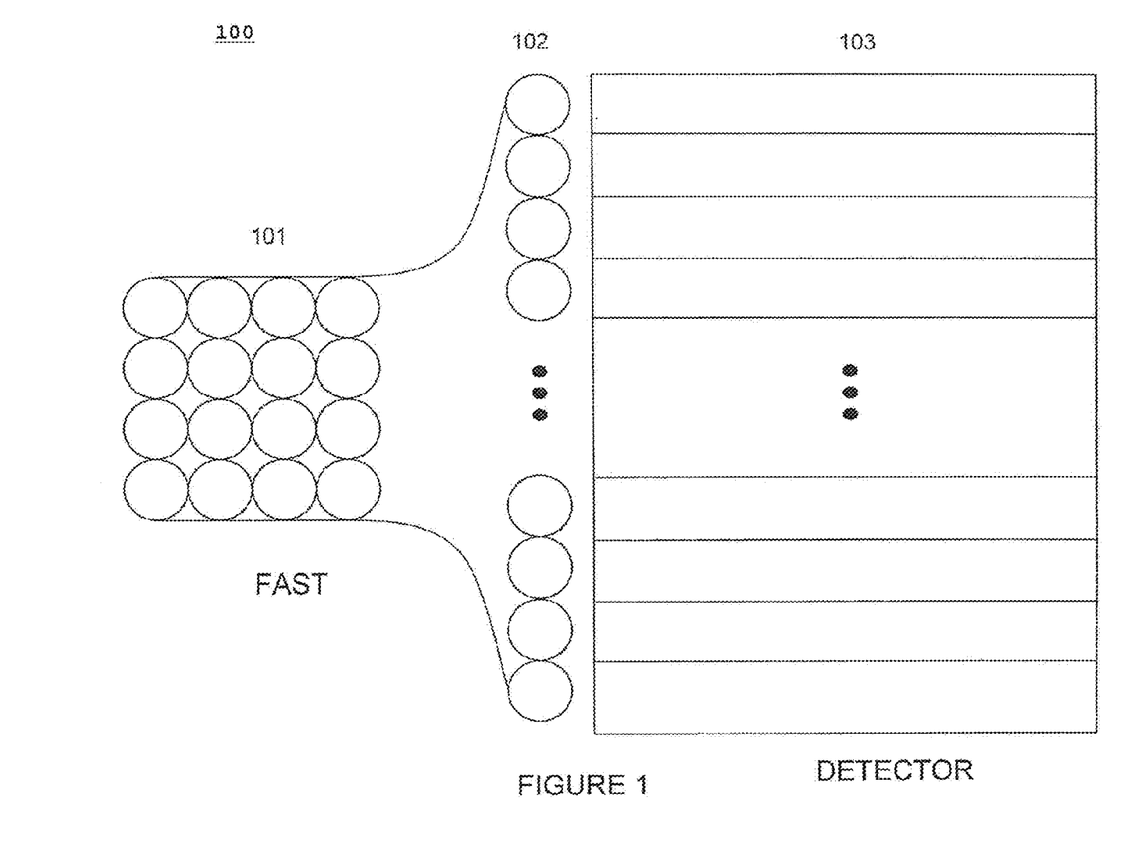
FIG. 1 is a schematic representation of a FAST device.

The construction of the FAST array requires knowledge of the position of each fiber at both the imaging end and the distal end of the array as shown, for example, in the diagram of FIG. 1 where a total of sixteen fibers are shown numbered in correspondence between the imaging end 101 and the distal end 102 of the fiber bundle. As shown in FIG. 1, a FAST fiber bundle 100 may feed optical information from its two-dimensional non-linear imaging end 101 (which can be in any non-linear configuration, e.g., circular, square, rectangular, etc.) to its one-dimensional linear distal end 102, which feeds the optical information into associated detector rows 103. The distal end may be positioned at the input to a photon detector 103, such as a CCD, a complementary metal oxide semiconductor ("CMOS") detector, or a focal plane array sensor (such as InGaAs, InSb, metal oxide semiconductor controlled thyristor ("MCT"), etc.). Photons exiting the distal end fibers may be collected by the various detector rows. Each fiber collects light from a fixed position in the two-dimensional array (imaging end) and transmits this light onto a fixed position on the detector (through that fiber's distal end).

Figure 2:
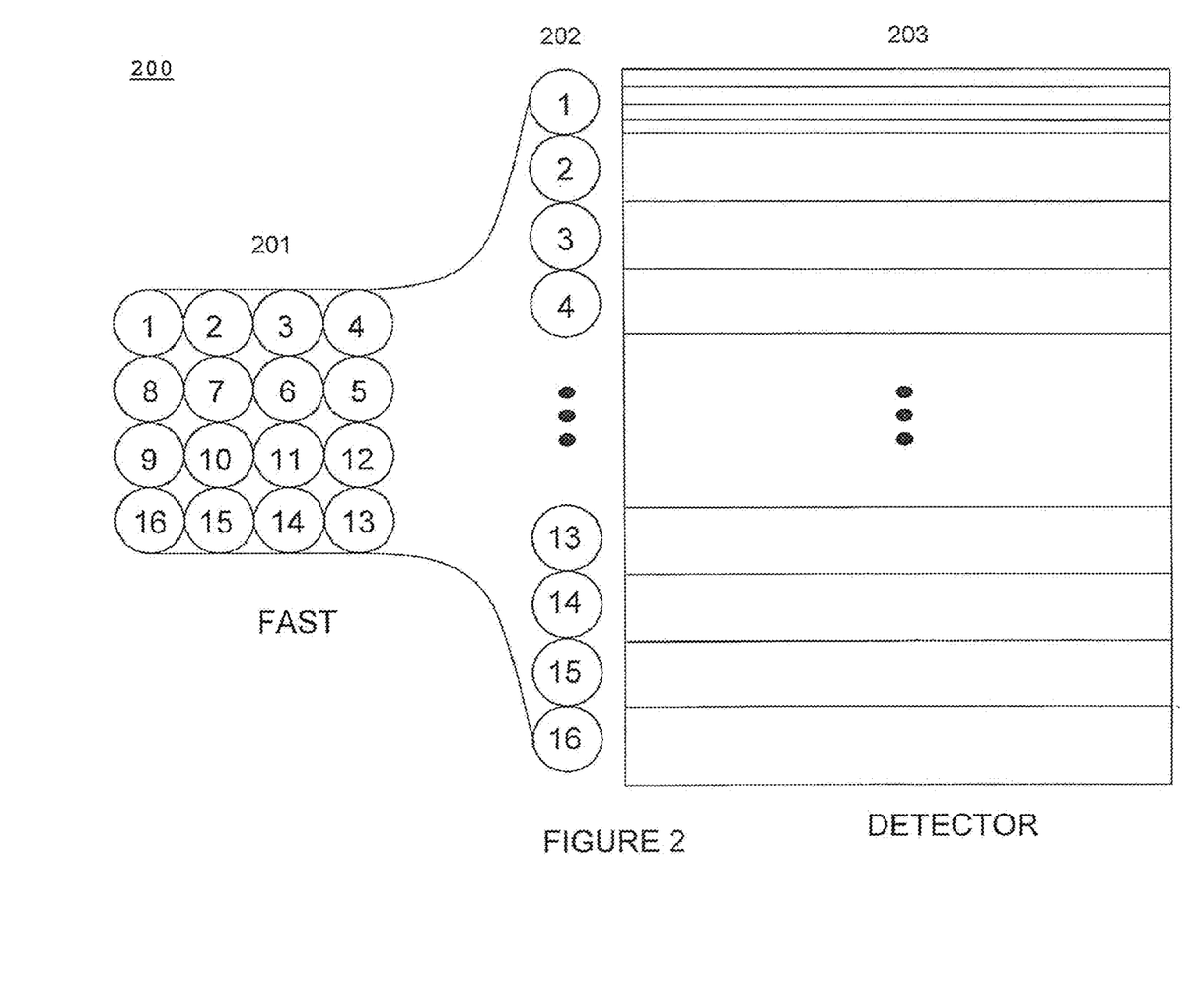
FIG. 2 is a schematic representation of a FAST device showing an exemplary spatial mapping arrangement.

FIG. 2 is a schematic representation of a non-limiting exemplary spatial arrangement of fibers at the imaging end 201 and the distal end 202. Additionally, as shown in FIG. 2, each fiber of the FAST fiber bundle 200 may span more than one detector row in detector 203, allowing higher resolution than one pixel per fiber in the reconstructed image. A system and method for spectral calibration of a spectroscopic system which includes a fiber array spectral translator is more fully described in U.S. Pat. No. 7,474,395, filed on Feb. 13, 2007 entitled, "System and Method for Image Reconstruction in a Fiber Array Spectral Translator System," which is hereby incorporated by reference in its entirety.

Figure 3:
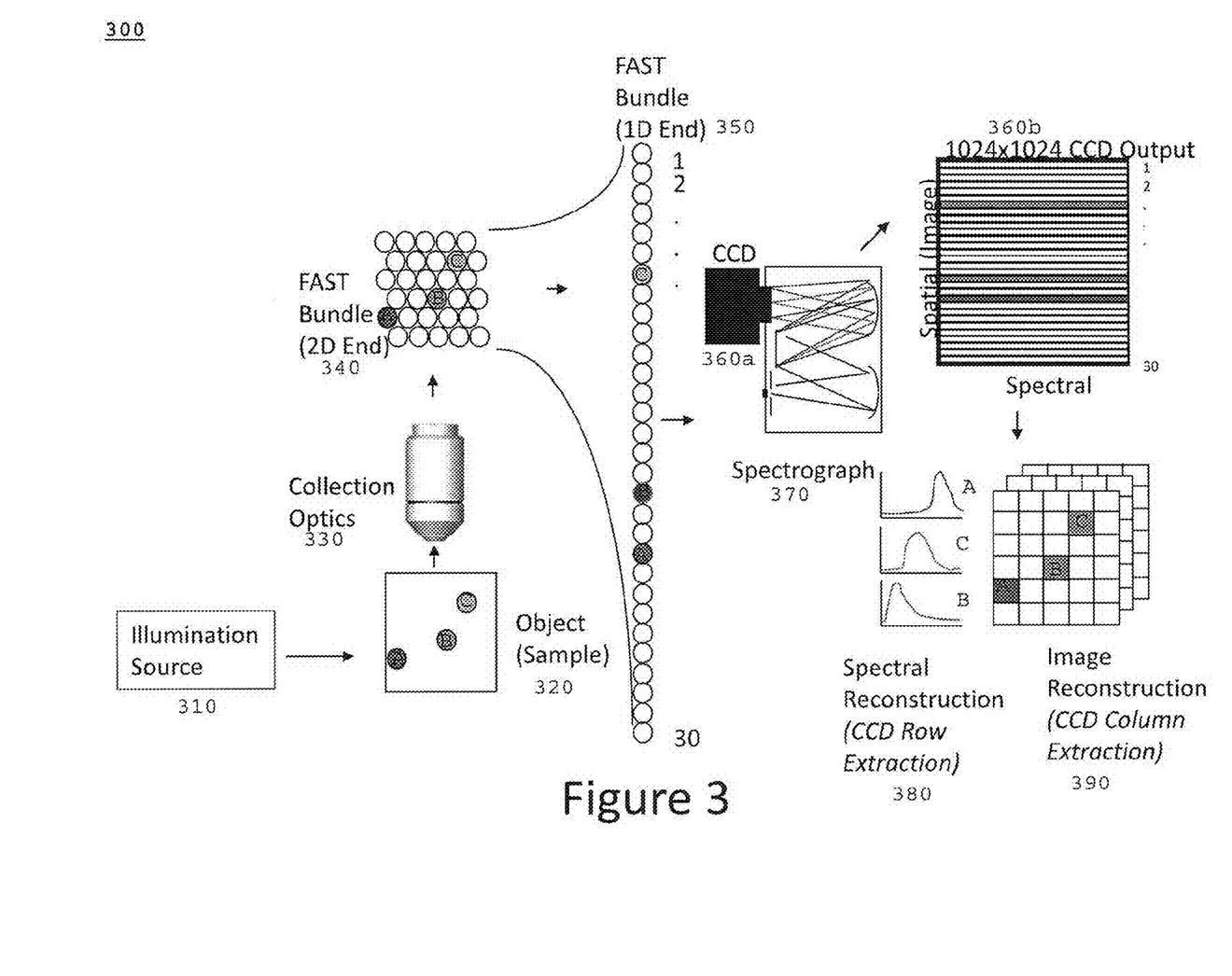
FIG. 3 is a schematic representation of a traditional FAST device.

FIG. 3 is a schematic representation of a system comprising a traditional FAST device. The knowledge of the position of each fiber at both the imaging end and the distal end of the array and each associated spectra is illustrated in FIGS. 3, 4, and 5 by labeling these fibers, or groups of fibers) A, B, and C.

The system 300 comprises an illumination source 310 to illuminate a sample 320 to thereby generate interacted photons. These interacted photons may comprise photons selected from the group consisting of: photons scattered by the sample, photons absorbed by the sample, photons reflected by the sample, photons emitted by the sample, and combinations thereof. These photons are then collected by collection optics 330 and received by a two-dimensional end of a FAST device 340 wherein said two-dimensional end comprises a two-dimensional array of optical fibers. The two-dimensional array of optical fibers is drawn into a one-dimensional fiber stack 350. The one-dimensional fiber stack is oriented at the entrance slit of a spectrograph 370. As can be seen from the schematic, the one-dimensional end 350 of a traditional FAST device comprises only one column of fibers. The spectrograph 370 may function to separate the plurality of photons into a plurality of wavelengths. The photons may be detected at a detector 360a to thereby obtain a spectroscopic data set representative of said sample. 360b is illustrative of the detector output, 380 is illustrative of spectral reconstruction, and 390 is illustrative of image reconstruction.

Figure 4:
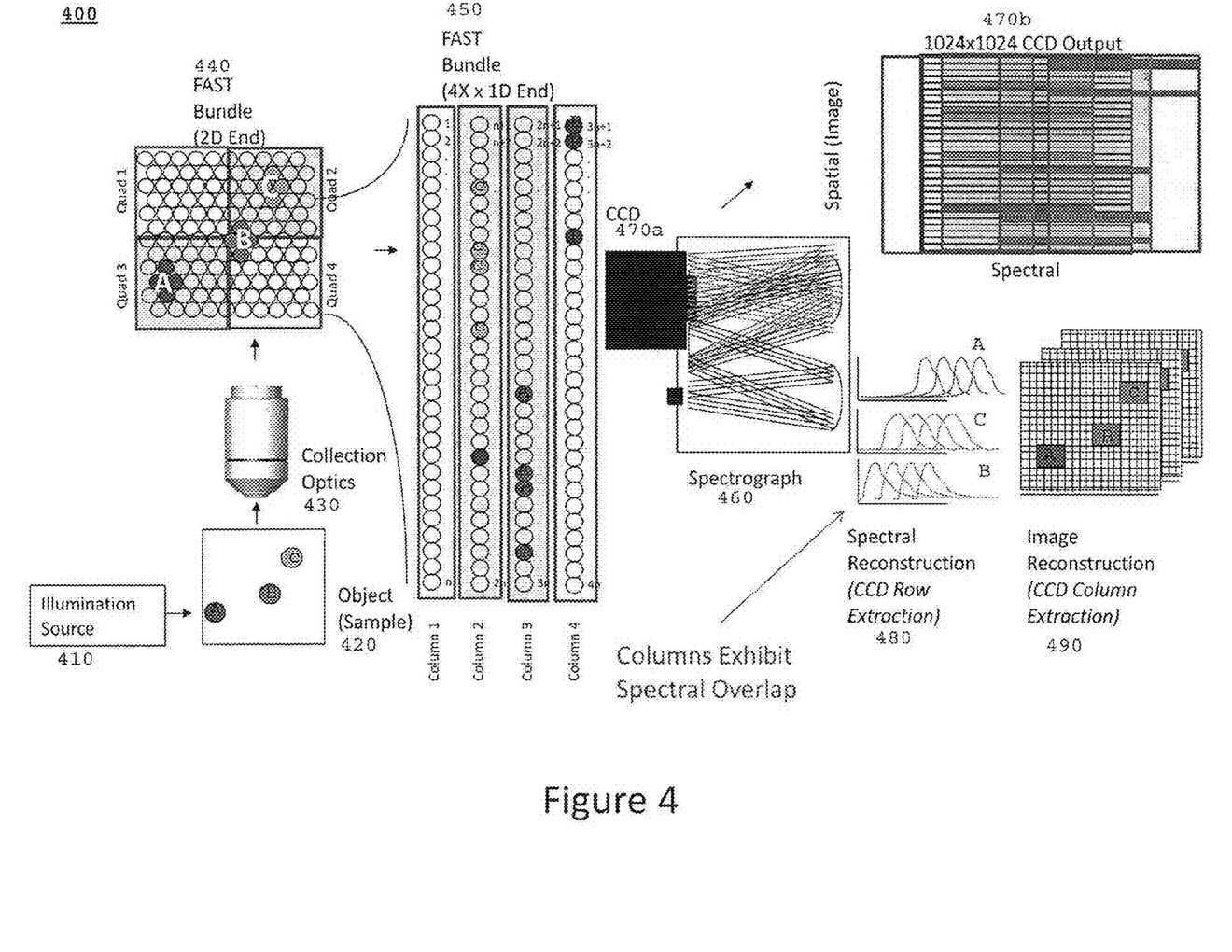
FIG. 4 is a schematic representation of a spatially parallelized FAST device.

FIG. 4 is a schematic representation of a system comprising a spatially parallelized FAST device. In FIG. 4, the system 400 comprises an illumination source 410 to illuminate a sample 420 to thereby generate interacted photons. These photons are collected by a collection lens 430 and received at a two-dimensional end 440 of a FAST device wherein said two-dimensional end comprises a two-dimensional array of optical fibers. The two-dimensional array of optical fibers is drawn into a one-dimensional fiber stack 450. As illustrated by FIG. 4, in an embodiment configured to provide for spatial parallelization of the FAST device, the one-dimensional end 450 may comprise at least two columns of fibers that are spatially offset in parallel at the entrance slit of a spectrograph 460. The spectrograph 460 may function to separate the plurality of photons into a plurality of wavelengths. The photons are detected at a detector 470a to thereby obtain a spectrographic data set representative of the sample. 470b is illustrative of the detector output. Although the embodiment of FIG. 4 allows for more fibers to be imaged at the entrance slit of the spectrograph 460, the embodiment also results in spectral overlap as illustrated by element 480. Element 490 is illustrative of image reconstruction.

Figure 5:
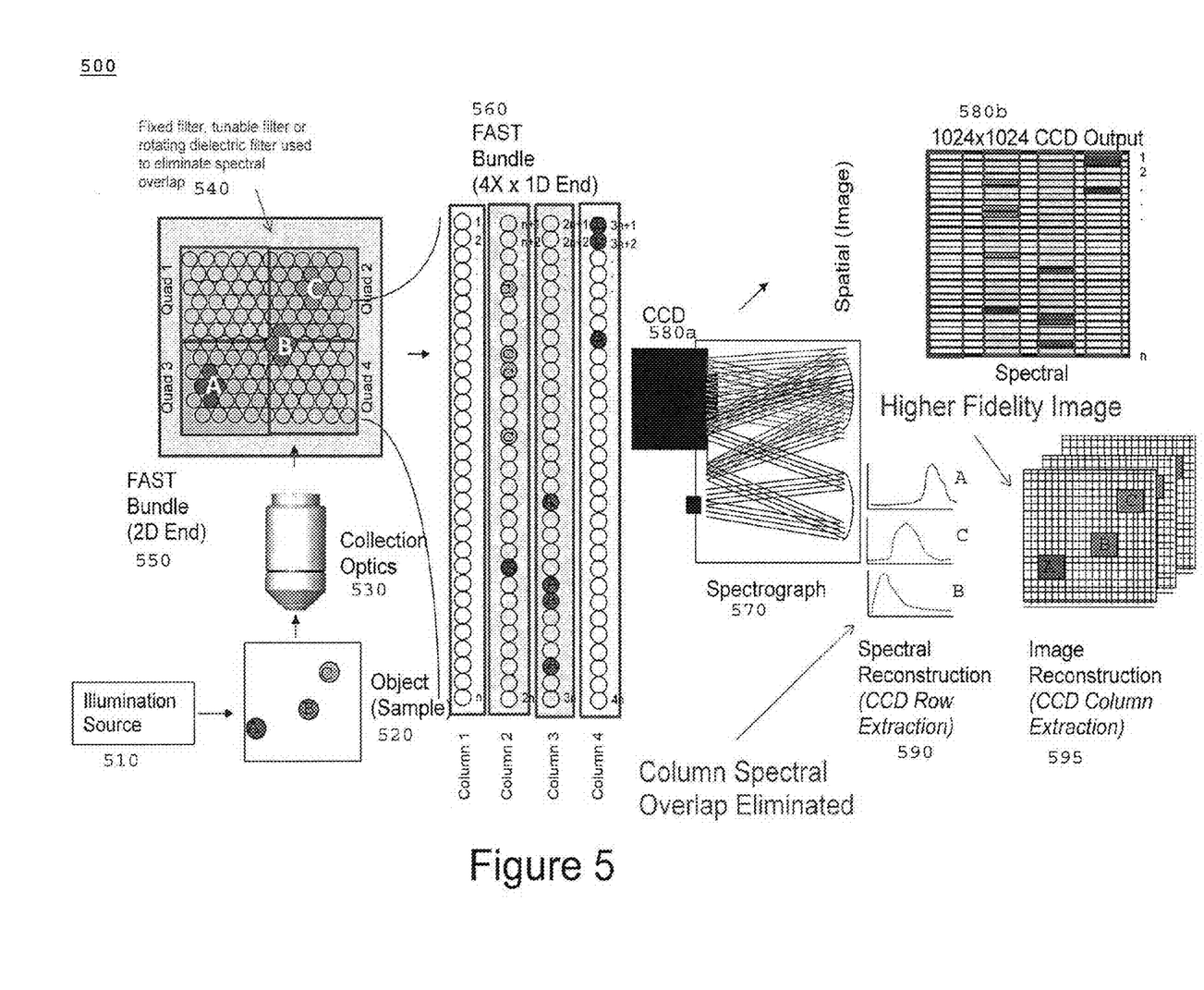
FIG. 5 is a schematic representation of one embodiment of the present disclosure illustrating a spatially and spectrally parallelized FAST device.

FIG. 5 is a schematic representation of an embodiment of the present disclosure. The system 500 comprises an illumination source 510 to illuminate a sample 520 to thereby produce interacted photons. These interacted photons may comprise photons selected from the group consisting of: photons scattered by the sample, photons absorbed by the sample, photons reflected by the sample, photons emitted by the sample, and combinations thereof. The interacted photons are collected by collection optics 530. The photons are passed through a filter 540 and delivered to a two-dimensional end of a fiber array spectral translator device 550 wherein said two-dimensional end comprises a two-dimensional array of optical fibers. The fiber array spectral translator device may comprise, in one embodiment, a two-dimensional array of optical fibers 550 drawn into a one-dimensional fiber stack 560 so as to effectively convert a two-dimensional field of view into a curvilinear field of view, and wherein said two-dimensional array of optical fibers 550 is configured to receive said photons collected by said optical lens 530 and transfer the received photons out of said fiber array spectral translator device and to a spectrograph 570 through said one-dimensional fiber stack 560. In the embodiment illustrated in FIG. 5, said one-dimensional fiber stack 560 comprises at least two columns of fibers spatially offset in parallel at the entrance slit of a spectrograph 570. In one embodiment, the spectrograph 570 may be used to separate the photons into a plurality of wavelengths. In one embodiment, the spectrograph 570 may comprise a dispersive spectrograph. The photons are detected at a detector 580a to thereby obtain a spectroscopic data set representative of said sample. Element 580b is illustrative of the detector output. As can be seen from the illustration 590, such an embodiment holds potential for eliminating the spectral overlap limitation of the prior art. Element 595 is illustrative of image reconstruction.

As illustrated in FIG. 5, the one-dimensional end of the FAST device 560 comprises multiple columns of fibers that are spatially offset in parallel at the entrance slit of a spectrograph 570. FIG. 5 also illustrates the use of a filter 540 to eliminate the spectral overlap limitations present in the prior art. In one embodiment, the filter 540 may comprise a filter selected from the group consisting of: a fixed filter, a rotating dielectric filter, a tunable filter, and combinations thereof. In one embodiment, the tunable filter may comprise a filter selected from the group consisting of: a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, a liquid crystal Fabry Perot tunable filter, a multi-conjugate tunable filter, and combinations thereof.

In one embodiment of the present disclosure, the system and method disclosed herein may comprise multi-conjugate filter technology available from ChemImage Corporation, Pittsburgh, Pa. Such technology is more fully described in U.S. Pat. No. 7,362,489, filed on Apr. 22, 2005, entitled "Multi-Conjugate Liquid Crystal Tunable Filter" and U.S. Pat. No. 6,992,809, filed on Feb. 2, 2005, also entitled "Multi-Conjugate Liquid Crystal Tunable Filter." These patents are hereby incorporated by reference in their entireties.

In one embodiment, said filter 540 may be positioned between said collection optics 530 and said two-dimensional end of said of FAST device 550 as illustrated in FIG. 5. In another embodiment, said filter may be positioned inside said spectrograph 570 after said the one-dimensional end of said FAST device 560.

Figure 6:
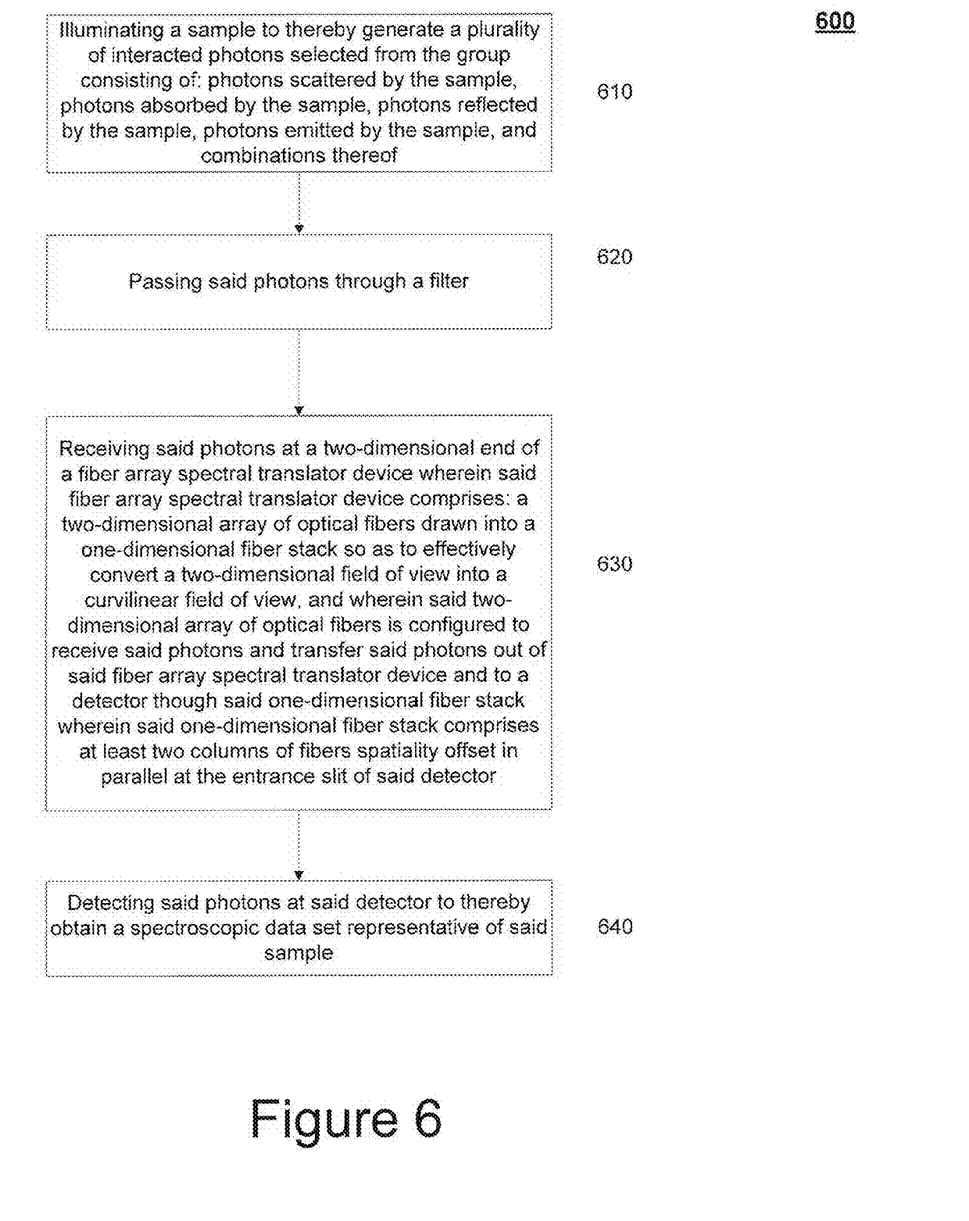
FIG. 6 is illustrative of a method of the present disclosure.

FIG. 6 illustrates a method of the present disclosure. The method 600 provides for illuminating a sample to thereby generate a plurality of interacted photons selected from the group consisting of: photons scattered by the sample, photons absorbed by the sample, photons reflected by the sample, photons emitted by the sample, and combinations thereof in step 610. In step 620 said photons are passed through a filter. The photons are received in step 630 at a two-dimensional end of a FAST device. In one embodiment, said FAST device comprises: a two-dimensional array of optical fibers drawn into a one-dimensional fiber stack so as to effectively convert a two-dimensional field of view into a curvilinear field of view, and wherein said two-dimensional array of optical fibers is configured to receive said photons and transfer said photons out of said fiber array spectral translator device and to a spectrograph through said one-dimensional fiber stack wherein said one-dimensional fiber stack comprises at least two columns of fibers spatially offset in parallel at the entrance slit of said spectrograph. In one embodiment, the spectrograph separates the photons into a plurality of wavelengths. In step 640 said photons are detected at a detector to thereby obtain a spectroscopic data set representative of said sample.

In one embodiment, each fiber of said FAST device is associated with a different predetermined region of said sample. In another embodiment, said predetermined region of said sample comprises a non-overlapping two-dimensional region wherein each said region includes a predetermined number of fibers. In yet another embodiment, at least two predetermined regions of said sample overlap.

In one embodiment, said filter through which said photons are passed comprises a filter selected from the group consisting of: a fixed filter, a tunable filter, a dielectric filter, and combinations thereof. In another embodiment, said filter may comprise a tunable filter selected from the group consisting of: a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, a liquid crystal Fabry Perot tunable filter, a multi-conjugate tunable filter, and combinations thereof.

In one embodiment, said detector may be any known in the art including a detector selected from the group consisting of: a charge-coupled device, a complementary metal oxide semiconductor detector, a focal plane array sensor, and combinations thereof.

In one embodiment, information extracted from the detector is extracted such that information corresponding to each quadrant of the two-dimensional end of the fiber array spectral translator device is extracted independently so that each quadrant has an associated image. In one embodiment, illustrated by FIG. 5, the two-dimensional end of the fiber array spectral translator device is divided into four non-overlapping regions or quadrants, each containing a predetermined number of fibers. Information corresponding to these four quadrants may be extracted from the detector to thereby generate four independent images, one representing each quadrant. These four images can then be combined to form an image representative of the entire two-dimensional end.

The present disclosure may be embodied in other specific forms without departing from the spirit or essential attributes of the disclosure. Although the foregoing description is directed to the embodiments of the disclosure, it is noted that other variations and modifications will be apparent to those skilled in the art, and may be made without departing from the spirit or scope of the disclosure.

What is claimed is:

1. A method comprising:
   illuminating a sample to thereby generate a plurality of interacted photons selected from the group consisting of: photons scattered by the sample, photons absorbed by the sample, photons reflected by the sample, photons emitted by the sample, and combinations thereof;
   passing said photons through a filter, wherein said filter is configured so as to effectively restrict the spectral range under analysis;
   receiving said photons at a two-dimensional end of a fiber array spectral translator device, wherein said fiber array spectral translator device comprises: a two-dimensional array of optical fibers drawn into a one-dimensional fiber stack so as to effectively convert a two-dimensional field of view into a curvilinear field of view, and wherein said two-dimensional array of optical fibers is configured to receive said photons and transfer said photons out of said fiber array spectral translator device and to a spectrograph through said one-dimensional fiber stack wherein said one-dimensional fiber stack comprises at least two columns of fibers spatially offset in parallel at the entrance slit of said spectrograph; and
   detecting said photons at a detector to thereby obtain a spectroscopic data set representative of said sample.

2. The method of claim 1 wherein each fiber of said fiber array spectral translator device is associated with a different predetermined region of said sample.

3. The method of claim 2 wherein said predetermined region of said sample comprises a non-overlapping two-dimensional region, wherein each said region includes a predetermined number of fibers.

4. The method of claim 2 wherein at least two predetermined regions of said sample overlap.

5. The method of claim 1 wherein said filter is selected from the group consisting of: a fixed filter, a tunable filter, a dielectric filter, and combinations thereof.

6. The method of claim 1 wherein said filter is selected from the group consisting of: a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, a liquid crystal Fabry Perot tunable filter, a multi-conjugate tunable filter, and combinations thereof.

7. The method of claim 1 wherein said detector is selected from the group consisting of: a charge-coupled device, a complementary metal oxide semiconductor detector, a focal plane array sensor, and combinations thereof.

8. A system comprising:
   an illumination source for illuminating a sample to thereby generate a plurality of interacted photons selected from the group consisting of: photons scattered by the sample, photons absorbed by the sample, photons reflected by the sample, photons emitted by the sample, and combinations thereof;
   a collection lens for collecting said interacted photons;
   a filter through which said photons are passed, wherein said filter is configured so as to effectively restrict the spectral range under analysis;
   a fiber array spectral translator device, wherein said fiber array spectral translator device comprises: a two-dimensional array of optical fibers drawn into a one-dimensional fiber stack so as to effectively convert a two-dimensional field of view into a curvilinear field of view, and wherein said two-dimensional array of optical fibers is configured to receive said photons and transfer said photons out of said fiber array spectral translator device and to a spectrograph through said one-dimensional fiber stack wherein said one-dimensional fiber stack comprises at least two columns of fibers spatially offset in parallel at the entrance slit of said spectrograph;
   a spectrograph for separating said photons into a plurality of wavelengths; and
   a detector for detecting said photons to thereby generate a spectroscopic data set representative of said sample.

9. The system of claim 8 wherein said filter is positioned between said collection optics and said two-dimensional end of said fiber array spectral translator device.

10. The system of claim 8 wherein said filter is positioned inside said spectrograph.

11. The system of claim 8 wherein said filter is selected from the group consisting of: a fixed filter, a tunable filter, a dielectric filter, and combinations thereof.

12. The system of claim 8 wherein said filter is selected from the group consisting of: a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, a liquid crystal Fabry Perot tunable filter, a multi-conjugate tunable filter, and combinations thereof.

13. The system of claim 8 wherein said detector is selected from the group consisting of: a charge-coupled device, a complementary metal oxide semiconductor device, a focal plane array sensor, and combinations thereof.

14. The method of claim 1 wherein said obtaining of said spectroscopic data set further comprises reconstructing an image representative of said sample.

15. The system of claim 8 wherein said detector is further configured so as to reconstruct an image representative of said sample.

\* \* \* \* \*

UNITED STATES PATENT AND TRADEMARK OFFICE
CERTIFICATE OF CORRECTION

PATENT NO. : 8,098,373 B2
APPLICATION NO. : 12/759082
DATED : January 17, 2012
INVENTOR(S) : Nelson et al.

Page 1 of 1

It is certified that error appears in the above-identified patent and that said Letters Patent is hereby corrected as shown below:

Col. 1, line 12
Please add the following paragraph as the second paragraph in the patent:

This invention was made with government support under W911NF-09-C-0078 awarded by US Army RDECOM. The government has certain rights in the invention.

Signed and Sealed this
Sixth Day of March, 2012

David J. Kappos
*Director of the United States Patent and Trademark Office*